United States Patent [19]

Slejko et al.

[11] 3,987,089

[45] Oct. 19, 1976

[54] PREPARATION OF β-ALKOXY ESTERS FROM OLEFINS

[75] Inventors: Frank L. Slejko, Bristol; James S. Clovis, Morrisville, both of Pa.

[73] Assignee: Rohm and Haas Company, Philadelphia, Pa.

[22] Filed: Oct. 21, 1974

[21] Appl. No.: 516,555

[52] U.S. Cl.................. 260/486 AC; 260/410.9 R; 260/468 M; 260/469; 260/473 A; 260/476 R; 260/479 R
[51] Int. Cl.² .......................................... C07C 9/54
[58] Field of Search ..... 260/486 AC, 410.9, 468 M, 260/469, 476 R

[56] References Cited
UNITED STATES PATENTS

| 2,876,254 | 3/1959 | Jenner et al. | 260/486 AC |
|---|---|---|---|
| 3,661,948 | 5/1972 | Schell | 260/486 AC |
| 3,681,415 | 8/1972 | Schell | 260/486 AC |
| 3,700,706 | 10/1972 | Butter | 260/486 AC |

OTHER PUBLICATIONS

J. Falbe, Carbon Monoxide in Organic Synthesis, 1967, pp. 99–105.

*Primary Examiner*—Paul J. Killos

[57] ABSTRACT

This invention discloses an improved process for the manufacture of $\alpha,\beta$-unsaturated carboxylic acid esters from a $\beta$-alkoxycarboxylic acid ester prepared by contacting an olefin having 2 to about 15 carbon atoms with an alcohol and carbon monoxide, where this alkoxycarbonylation reaction is performed with mutually independent improvements which include (A) reacting the compounds in the presence of a catalyst having as the major catalytic agent a salt of a platinum group metal and as a co-catalyst a salt of a metal selected from the group consisting of mercury (II) and tin (II), with a reoxidizing agent which is a salt of a multivalent metal having an oxidation potential more positive than the platinum group metal salt, (B) performing the reaction in an improved solvent system comprising the monohydric alcohol, the $\beta$-alkoxycarboxylic acid ester and a solvent having a boiling point higher than that of the $\beta$-alkoxycarboxylic acid ester, (C) reoxidizing the catalyst prior to isolation of the $\beta$-alkoxycarboxylic acid ester from the reaction medium, and (D) cracking the $\beta$-alkoxycarboxylic acid ester to the corresponding $\alpha,\beta$-unsaturated carboxylic acid ester.

13 Claims, 1 Drawing Figure

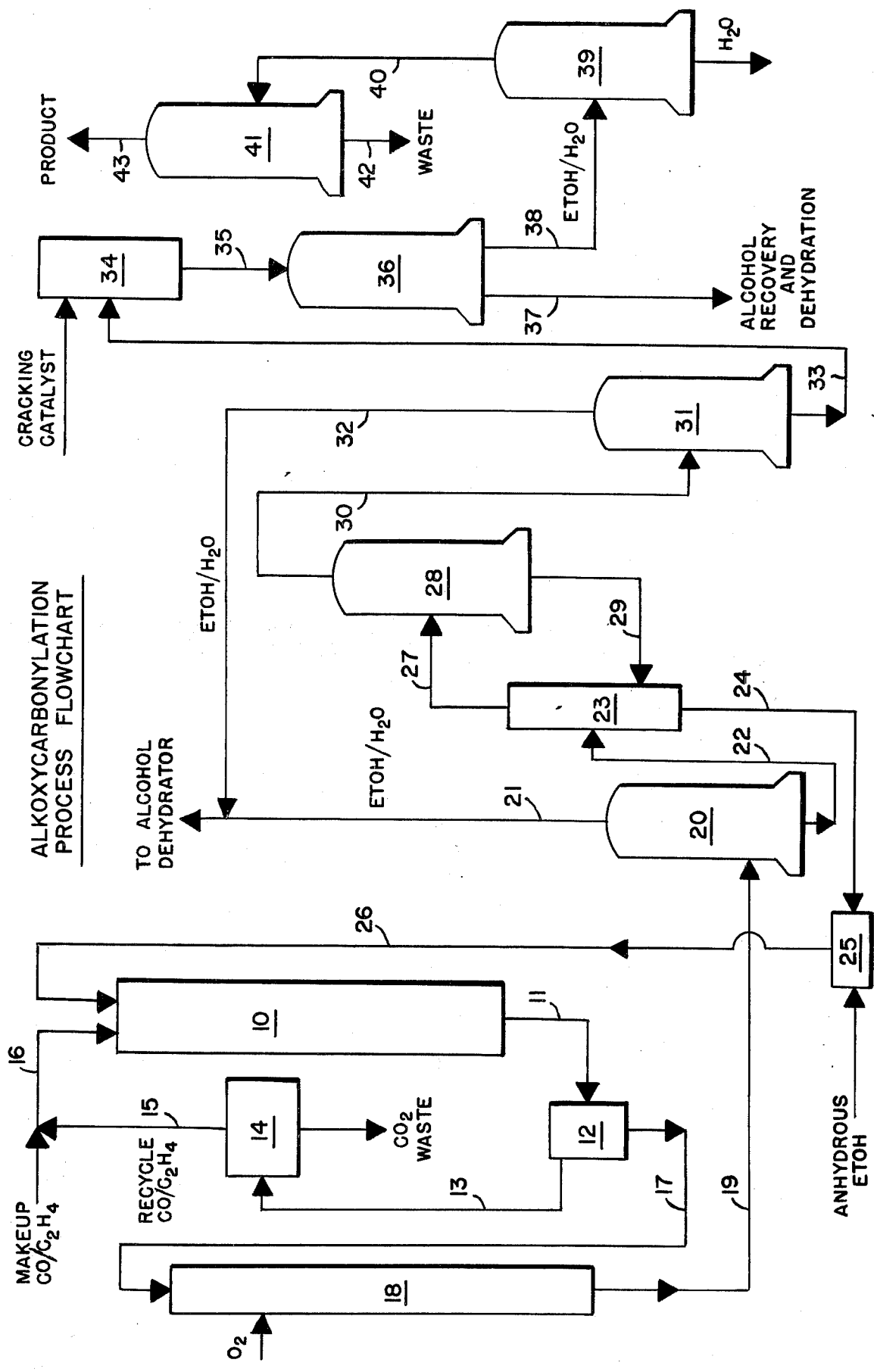

PREPARATION OF β-ALKOXY ESTERS FROM OLEFINS

This invention relates to an improved process for the preparation of α,β-unsaturated carboxylic acid esters from β-alkoxycarboxylic acid esters prepared by reaction of an olefin, an alcohol and carbon monoxide in a solvent system and in the presence of a catalyst.

The alkoxycarbonylation process for the production of unsaturated acid esters from an olefin, a monohydric alcohol and carbon monoxide has been disclosed and is claimed in the Fenton patent, U.S. Pat. No. 3,397,225. However, while the process, as described by Fenton, is workable, a number of serious problems make it unfeasible for a commercial level of ester production.

One of the major drawbacks of the Fenton process is the fact that α,β-unsaturated carboxylic acid esters are not produced during the alkoxycarbonylation reaction as claimed by Fenton. In repeated efforts to duplicate the results claimed by Fenton, a reaction involving methanol, carbon monoxide and ethylene did not produce any significant quantity of methyl acrylate. Instead, gas-liquid chromotography showed large quantities of methyl propionate and some methyl β-methoxypropionate. It is conceivable that methyl propionate was misidentified as methyl acrylate, as the two compounds are very difficult to separate by gas-liquid chromotography employing standard columns and techniques. Separation of methyl acrylate from methyl propionate by gas-liquid chromotography was effectuated by using a 20 foot long by ⅛ inch diameter column of 20% UCON -50-HB 2000X coated onto a Firebrick R 40–60 mesh support. A 5 foot long by ⅛ inch diameter column of 5% FFAP coated onto a POROPACK Z 50–80 mesh support did not permit the resolution afforded by the above-mentioned column. It appears, therefore, that the columns generally in use in gas-liquid chromotography will not separate methyl propionate from methyl acrylate, and misidentification of propionate for acrylate is highly probable. It is also postulated that inadvertently some of the β-methoxypropionate may have been cracked to methyl acrylate during a distillation step, although no such cracking was found to occur upon duplication of the examples in the Fenton patent. In the event that α,β-unsaturated esters were to be produced in one step, difficulties would nevertheless ensue. In particular, difficulty would be encountered in separations of unreacted alcohol and low boiling impurities from product, as well as problems with polymerization of the product. Since α,β-unsaturated carboxylic acid esters are not produced directly, and β-alkoxycarboxylic acid esters are, a commercially attractive process must involve maximization of β-alkoxycarboxylic acid ester yield, elimination, at least to the greatest extent possible, of undesirable by-products, and extension of the complete process to include production of α,β-unsaturated carboxylic acid esters from the β-alkoxycarboxylic acid esters.

Another undesirable feature of the Fenton process is the fact that the alkoxycarbonylation reaction and regeneration of catalyst proceeds with the formation of a number of by-products which include carbon dioxide, and various undesirable organic compounds such as unsubstituted saturated esters, succinate esters, β-chlorosubstituted esters, acetaldehyde, acetals, etc. Carbon dioxide is formed by the oxidation of carbon monoxide, both during the alkoxycarbonylation reaction and during catalyst regeneration. Water present in the system is believed to promote carbon dioxide formation during the alkoxycarbonylation step.

When the Fenton process catalyst salts are chlorides, hydrogen chloride is formed in the alkoxycarbonylation step during the reoxidation of the platinum group metal by the multivalent metal chloride. It has been found that if the formation of unsubstituted saturated propionate esters is minimized, as by increasing the reaction temperature, the hydrogen chloride in the system reacts with the alcohol to produce water and undesirable by-products such as ethers and alkyl halides, with the water, in turn, aiding in the further formation of carbon dioxide. Additionally, in the Fenton process, catalyst regeneration is carried out after first removing the product from the catalyst/reactants mixture. However, removal of product by distillation in the presence of hydrogen chloride leads to still further by-product formation including product hydrolysis.

Also linked to high hydrogen chloride levels is the formation of highly undesirable saturated unsubstituted esters. Thus, when the olefin is ethylene and methanol is the alcohol, methyl propionate formation occurs preferentially in the presence of high hydrogen chloride levels. The desired product is the substituted ester i.e., methyl β-methoxypropionate, which is readily cracked to produce its corresponding α,β-unsaturated carboxylic acid ester. Thus, high levels of hydrogen chloride are a further factor in the preferential formation of saturated unsubstituted esters over the desired β-alkoxy esters.

In addition to the foregoing drawbacks, the Fenton process is carried out under reaction conditions which aid in by-product formation. Fenton prefers a feed composition using large excesses of carbon monoxide over olefin. However, higher carbon monoxide concentrations serve only to enhance carbon dioxide formation. Fenton also prefers reaction temperatures from about 100° to about 225° C. These temperatures are conducive to alcohol dehydration with the resulting problems of formation of water, ethers, alkyl halides, carbon dioxide, and so forth. Fenton preferentially employs an excess of a monohydric alcohol as the reaction medium. However, this is undesirable for several reasons. The first problem is that distillation of the dilute alcoholic solution of products from the catalyst system necessitates heating the catalysts virtually to dryness in order to remove all of the water and product. The high temperatures required to accomplish this would promote by-product formation and product decomposition. Secondly, even with high levels of multivalent metal chloride reoxidant, for example, only dilute solutions of product in alcohol are obtained. This requires costly separation steps to remove the large quantities of alcohol from the product. Finally, the solid catalyst remaining after the distillation would require impractical handling techniques for recycling. Failure to recycle the catalyst efficiently would make the entire process economically unworkable.

It is clear, therefore, that the process as disclosed by Fenton is not commercially sound. The Fenton process cannot advantageously be used to form acrylic acid esters and other unsaturated carboxylic acid esters in one step, since the Fenton process (a) does not produce the unsaturated carboxylic acid esters in one step, and (b) the useful β-alkoxycarboxylic acid esters that are produced are formed along with significant amounts of undesirable by-products. The mutually independent improvements of this present invention, however, overcome the undesirable features of the Fenton process and make it possible to produce α,β-unsaturated carboxylic acid esters in high yields in an economically advantageous alkoxycarbonylation process.

One significant improvement over the Fenton process resides in the makeup of the alkoxycarbonylation catalyst. As has been indicated above, the use of a platinum group metal salt and a multivalent metal salt, such as palladium chloride catalyst and cupric chloride reoxidant results in formation of relatively large quantities of saturated unsubstituted esters, such as methyl propionate. Increase of temperature during the reaction suppresses the formation of undesired esters, but leads to alcohol dehydration by the hydrogen chloride. In the present invention, the addition of a mercuric salt co-catalyst to the basic platinum group metal salt/multivalent metal salt catalyst system results in an unexpected suppression of saturated, unsubstituted esters, while selectivity to β-alkoxycarboxylic acid esters is enhanced with resultant large yields by use of mercuric or stannous salts. The mechanism by which the mercuric or stannous salt operates is not well understood, but it is believed that an intermediate complex may possibly be involved in the increased selectivity of formation of the β-alkoxy esters as opposed to unsubstituted saturated esters. This is of crucial importance, as the formation of unsubstituted saturated esters serves only to seriously decrease yields of the β-alkoxy esters.

A further improvement of the reaction is the solvent system in which the alkoxycarbonylation is run. The Fenton process uses either an excess of monohydric alcohol as the reaction medium, or a system using other solvents such as ethers, esters, saturated hydrocarbons and so forth. As indicated, such systems can lead to costly by-product formation, product decomposition, catalyst recycle problems, etc. The present invention provides an improved solvent system which overcomes the undesirable aspects of an all-alcohol or other organic solvent system. More particularly, the above-mentioned problems can be avoided by having a solvent which: (a) does not react to form by-products during the reaction, (b) is higher boiling than the β-alkoxy-substituted ester, and (c) helps solubilize or aid in slurrying the catalyst. Many compounds fit this description, but the most suitable are the high boiling sulfones, such as sulfolane. The β-alkoxy carboxylic acid ester can also be employed as a high boiling solvent for the reaction, however, the catalyst is essentially insoluble in the β-alkoxy-substituted esters. On the other hand, the catalyst is somewhat soluble in sulfolane. Thus, by using a sulfolane-based solvent system, product, water, by-products and unreacted starting materials can be readily separated from the catalyst system and high boiling solvent by simple distillation. The catalyst is somewhat dissolved or at least suspended in the high boiling solvent composition, making catalyst recycle feasible. The β-alkoxy-substituted esters can be used as a co-solvent along with the high boiling sulfones and alcohol. One advantage in using the β-alkoxy esters as a co-solvent is that a highly pure grade of α,β-unsaturated esters can be achieved. Thus, an acceptable sulfone, such as sulfolane, permits the initial separation of catalyst from reaction mixture. Subsequently, by-products boiling in the range of the desired α,β-unsaturated ester, for example such as methyl propionate and 1,1-dimethoxyethane in a range with methyl acrylate, can be easily separated from the β-alkoxy-substituted ester, such as methyl β-methoxypropionate, by a simple distillation. By-products boiling close to the β-alkoxy derivative, such as methyl β-chloropropionate, can be easily separated as high boilers after cracking the β-alkoxy derivative to the corresponding α,β-unsaturated ester. The result is that very pure α,β-unsaturated esters are produced based upon simple fractionation.

While the basic alkoxycarbonylation reaction is highly important, an equally critical aspect of the whole process is the catalyst regeneration step. If the catalyst cannot be readily and effectively regenerated and then recycled in a continuous manner the entire process will not be economically feasible. As indicated, Fenton regenerates the catalyst after separation of the product from the reaction zone. As large quantities of hydrogen chloride are present in solution at this point, removal of product in the presence of hydrogen chloride gives rise to considerable by-product formation, in particular, hydrolysis of the product to saturated β-alkoxycarboxylic acids occurs under these conditions. It was found, however, that by regenerating the catalyst prior to produce recovery, by-product formation during this step can be effectively prevented. Thus, during the improved regeneration, CuCl and HCl react with oxygen to form $CuCl_2$ and $H_2O$. As a result, the product is distilled from a hydrogen chloride-free solution and by-product formation is avoided.

The present improved process also incorporates certain reaction paarameters which have been found to enhance product yields and suppress by-product formation. By carrying out the alkoxycarbonylation reaction at a temperature within the range of 10° to 80° C., a number of distinct advantages can be realized. Alcohol dehydration and related alcohol side reactions are minimized, which in turn helps to minimize carbon dioxide formation. Likewise, premature cracking of the β-alkoxycarboxylic acid esters is prevented by a low temperature reaction. Also, changing the gaseous feedstream to achieve a ratio of olefin to carbon monoxide of 3:1 results in considerably less carbon dioxide formation and enhances complete reaction to the desired β-alkoxy esters. It has also been found that by increasing the levels of reoxidant to catalyst, such as a ratio of about 100:1, succinate ester formation is significantly reduced. Additionally, carrying out the alkoxycarbonylation reaction in the absence of oxygen results in complete suppression of acetaldehyde and acetal formation.

The attached drawing is a flowsheet of the improved process showing the continuous manner in which α,β-unsaturated carboxylic acid esters are prepared, and depicting the production of ethyl acrylate from ethanol, ethylene and carbon monoxide.

Carbon monoxide, anhydrous ethanol, ethylene, and catalyst in sulfolane are reacted in the primary reactor 10, the reacted mixture and catalyst being cycled via 11 to a liquid-gas separator 12, in which waste carbon dioxide and unreacted carbon monoxide and ethylene are vented via 13 from the catalyst and crude product mixture. The vented gases are separated in 14 with waste carbon dioxide being removed and unreacted carbon monoxide and ethylene being recycled via 15 and 16 back to the primary reactor for further reaction. The crude product and catalyst mixture is run via 17 into the catalyst regenerator 18 were regeneration is carried out with oxygen. The regenerated catalyst is then fed via 19 to flash evaporator still 20, wherein water and unreacted ethanol are removed and sent via 21 to an alcohol dehydrator. The crude product/catalyst slurry is then fed via 22 to a sulfolane extractor 23 where the regenerated catalyst slurry is extracted with dry sulfolane to remove the remaining water. The catalyst is mixed with anhydrous ethanol in 25 via 24, then it is recycled to the primary reactor 10 via 26. The crude product is sent to a sulfolane recovery still 28 via 27 in order to separate crude product and water from remaining sulfolane, the latter being recycled via 29 back to the sulfolane extractor 23. Crude product separated from sulfolane is sent to a product recovery still 31 via 30 wherein remaining water and unreacted ethanol are recovered and sent via 32 to the alcohol dehydrator while the ethyl β-ethoxypropionate is sent via 33 to the dealkoxylation or cracking unit 34. The ethanol and crude ethyl acrylate formed by the cracking step are transferred via 35 to distillation unit 36, where the ethanol and water are removed and sent via 37 to alcohol recovery and dehydration. The crude product and remaining water are sent via 38 to another distillation unit 39 where the remaining water is removed from the crude ethyl acrylate, the latter being sent via 40 to a final fractional distillation unit 41 to separate ethyl acrylate 43 from waste products 42.

The present improved process for production of α,β-unsaturated carboxylic acid esters involves the following steps and improvements therein.

An olefin of the formula:

$$R_1-CH=CHR_2$$

where $R_1$ and $R_2$ can be hydrogen, alkyl, aryl, alkaryl, or aralkyl, and the total number of carbon atoms in the olefin is from about 2 to 15, and carbon monoxide are contacted with alcohol of the formula:

$$X-R_3OH$$

where $R_3$ is alkyl, aryl, alkaryl, aralkyl and where the number of carbon atoms is from about 1 to 10 and X is hydrogen or a hydroxyl group, in the presence of a catalyst comprising a salt of a platinum group metal in an elevated oxidation state, preferably a salt of mercury (II) or tin (II) as a co-catalyst, and an additional salt of a multivalent metal having an oxidation potential more positive than the platinum group metal, in the absence of oxygen at a temperature from about 0° to about 85° C. and a pressure from about 75 to about 800 pounds per square inch gauge (p.s.i.g.) in a solvent system comprising said alcohol, said β-alkoxycarboxylic acid ester and a high boiling sulfone such a sulfolane. Upon completion of reaction, the reaction mixture is treated with an oxygen containing gas at a temperature of 0° to about 250° C. and a pressure from atmospheric to about 1500 pounds per square inch gauge in order to regenerate the catalyst. Subsequent to regeneration, the product, unreacted alcohol and by-products are distilled from the reaction mixture leaving the catalyst mixture dissolved or at least suspended in the high boiling sulfone. After separation of product from by-products and unreacted alcohol by conventional distillation methods, the β-alkoxycarboxylic acid ester is cracked to produce the corresponding α,β-unsaturated carboxylic acid ester.

Any olefin having 2 to about 15 carbon atoms can be used, and typical useful olefins are: ethylene, propylene, butene-1, butene-2, isobutene, pentene-1, pentene-2, 2methylbutene-1, 2-methylbutene-2, cyclopentene, hexene-1, hexene-2, hexene-3, cyclohexene, 2-ethylbutene-1, 2-methylpentene-1, heptene-3, 2-ethylhexene-3, cycloheptene, 1-methylcyclohexene, 1-octene, isooctene, 1-decene, 1-butylcyclohexene, 1,3-diethylcyclohexene, isodecene, indene, styrene, α-methylstyrene, allylbenzene, etc. The olefin feed can vary from about 50% to 75% of the total feed, with carbon monoxide varying from about 25% to 50%. A preferable feed has about 75% olefin to about 25% carbon monoxide, as such a feed does not give rise to as much carbon dioxide as a feed having large excesses of carbon monoxide over olefin.

An alcohol having 1 to about 10 carbon atoms is used, and typical examples are: methanol, ethanol, propanol, isopropanol, butanol, isobutanol, pentanol, isopentanol, hexanol, heptanol, octanol, nonyl alcohol, decanol, cyclohexanol, cyclopentanol, ethylene glycol and the like. Likewise, phenol, naphthol, meta-cresol, para-cresol, xylenol and similar aromatic hydroxy compounds can be used.

The unique catalyst system of catalyst, co-catalyst and a reoxidant is the major factor in reducing undesirable ester formation and enhancing β-alkoxy ester production. The platinum group metal may be of the platinum sub-group, such as platinum, rhodium or ruthenium, or of the palladium sub-group, such as palladium, uranium or osmium. Because of its particular activity in the alkoxycarbonylation reaction, palladium is the preferred catalyst. It may be used at levels between 0.01 to 5.0 weight percent of total solution, preferably between 0.1 and 1.0 weight percent of total solution. While larger quantities may be used, there is no economic advantage in doing so. The catalyst is used as a soluble salt or as a chelate, and examples thereof include the halides, sulfates, nitrates and salts of the lower ($C_1$–$C_5$) carboxylates, and chelates such as the acetylacetonates and complexes with citric acid, ethylene diamine tetraacetic acid, etc.

The co-catalyst to the platinum group metal salt can be a compound of mercury (II) or tin (II). Again, a variety of salts and chelates can be used, such as halides, sulfates, nitrates, acetates, acetylacetonates, complexes with ethylene diamine tetraacetic acid, etc. In particular, the chlorides have been found to be most preferred. If halides are used as the main catalyst and reoxidant, it is postulated that the ultimate mercury (II) or tin (II) compound in solution is likewise a halide, in spite of the nature of the original compound employed. The ratio of mercury or tin to platinum group metal may be 0.1:1 to 50:1, preferably between 2:1 to 5:1.

A reoxidant is employed to return the platinum group metal to its original oxidation state from its reduced state, said metal being reduced during the alkoxycarbonylation reaction. In general, a salt of any multivalent metal having an oxidation potential more positive than the platinum metal can be used. Typical useful soluble salts include the $C_1$ to $C_5$ fatty acid carboxylates, nitrates, sulfates, halides and so forth of multivalent metals such as copper, iron, manganese, cobalt, nickel, bismuth, chromium, molybdenum, cerium, vanadium and the like. Of these, cupric and ferric salts are preferred and cupric salts most preferred. The cupric compound may be used at levels between 1.0 and 50.0 weight percent of total solution preferably between 5 and 25 weight percent. It is emphasized that a large excess of reoxidant over platinum group metal is essential in order to suppress formation of succinate esters as well as to reoxidize the platinum group metal. Thus, weight ratios of reoxidant to catalyst may be as high as 130:1.

The reaction can be performed at temperatures from about 0° to about 250° C. However, the lower the temperature the less likely is the possibility of reacting the alcohol to form alkyl halides and ethers. Most importantly, although higher temperatures help to reduce formation of unsubstituted saturated esters, use of the mercury salt as co-catalyst entirely suppresses formation of these esters even at ambient temperatures, and thereby allows a lower reaction temperature to be employed. Additionally, lower temperatures minimize the possibility of premature cracking of the $\beta$-alkoxy ester to the corresponding $\alpha,\beta$-unsaturated compound. Consequently, it has been found that the alkoxycarbonylation can be readily carried out at temperatures in the range of about 10° to about 85° C. and a preferred range of about 25° to about 75° C. The pressures used are sufficiently high to increase solubility of the gaseous reactants in the liquid reaction medium. While Fenton prefers a pressure of 500 to about 2500 pounds per square inch gauge, the improved process is preferably carried out at a pressure of about 100 to about 800 p.s.i.g., with a preferred range of about 150 to about 600 p.s.i.g. Equally important is the fact that the alkoxycarbonylation catalyst system is extremely corrosive to metals such as stainless steels, and plastics, such as polytetrafluoroethylene are used to line reaction vessels to overcome this problem. Such plastic liners, however, do not withstand high pressures very well, and lower pressures are helpful in order to make use of such a corrosion preventing system.

The solvent system employed can be a combination of the alcohol, the $\beta$-alkoxyesters and a high boiling solvent. The alcohol may be any of those already discussed in connection with the alcohol used in the reaction itself. The $\beta$-alkoxycarboxylic acid ester used would be the one being produced by the reaction. The high boiling solvent is any solvent which meets the criteria of a high boiling solvent as set out supra, and useful examples include sulfones, glycol ethers, nitriles, amides, aromatic amines and sulfoxides. The most useful and the preferred are the sulfones, with tetramethylenesulfone or sulfolane being the most preferred, as it has a boiling point about 100° C. higher than methyl $\beta$-methoxypropionate, is inert under reaction conditions, aids in solubilizing $CuCl_2$ and CuCl and is easily purified by distillation (B.P. 77° C. at 8mm Hg). While Fenton uses either an excess of alcohol or another solvent, the alcohol or solvent alone does not provide all the benefits that a combined solvent system does, as was discussed supra. Thus, since the purpose of the high boiling solvent is to help fluidize the otherwise solid catalyst and so permit it to be recycled, as well as to help provide a fractionable product recovery system, the amount of high boiling solvent used must be sufficient to meet both purposes. A solvent fitting these requirements is one which has about 30 to 200 parts of high boiling solvent per 100 parts of alcohol. A preferred system additionally includes about 25 to 85 parts of $\beta$-alkoxycarboxylic acid ester per 100 parts of alcohol.

The step of regenerating the catalyst is preferably performed prior to any catalyst/reactants separation and is carried out using oxygen and/or air. The reaction is pressurized with the gases to a pressure of from about atmospheric to about 1500 p.s.i.g. at ambient temperature. The procedure completely regenerates the catalyst and may be run in a continuous fashion, as well as in batches. It is interesting to note that in a sulfolane-containing solvent system catalyst regeneration is feasible even if there is a 100% reduction of the reoxidant metal to its lowest oxidation level above zero valence during the alkoxycarbonylation reaction. In a system not having sulfolane, such a 100% reduction results in precipitation of the platinum group metal and regeneration of that metal to the desired oxidation state proceeds with great difficulty.

Product recovery can be carried out by an initial solvent extraction or distillation of product, reaction by-products and unreacted compounds from sulfolane and catalyst. The fluidized or slurried regenerated catalyst/sulfolane system can be recycled, allowing the process to be run continuously. The extract of distillate is then fractionally distilled to remove by-products and unreacted compounds from product. Any by-products not separated in this distillation step can be separated fractionally after the $\beta$-alkoxy ester is cracked.

The cracking of the $\beta$-alkoxycarboxylic acid ester to obtain the corresponding $\alpha,\beta$-unsaturated carboxylic acid ester may be carried out according to known procedures. Typical cracking procedures generally involve the use of various catalysts. U.S. Pat. No. 3,022,338 discloses cracking over a catalyst of an alkaline earth metal phosphate and a compound of an element selected from copper, cerium, thorium, vanadium, chromium, iron and nickel. U.S. Pat. No. 3,031,493 discloses a catalyst of silica and a compound selected from the group consisting of group IVA and VA metal oxides, alkali metal silicates and alkaline earth metal silicates. U.S. Pat. No. 3,022,339 discloses the use of a boron phosphate catalyst. U.S. Pat. No. 3,227,746 discloses the use of dehydration catalysts such as sulfuric acid, phosphoric acid, halogenated sulfuric and phosphoric acids, and the like. Nevertheless, no particular cracking method is required and the above listed methods of cracking are to be deemed as merely representative, with other methods occuring to practitioners of the art.

Subsequent treatment of the $\alpha,\beta$-unsaturated carboxylic acid ester produced during the cracking step can include further fractional distillation, in the presence of suitable polymerization inhibitors when needed, to remove high boiling by-products and thereby achieve a highly pure product. The catalyst, as well as unreacted alcohol and all other recoverable materials can be recycled in order to achieve a continuous alkoxycarbonylation process.

While theories and manufacturing methods have been disclosed, it is not meant that the invention is to be limited to any of these theories and methods, as other equally valid theories and alternative methods may exist within the framework of the improved process for production of $\alpha,\beta$-unsaturated carboxylic acid esters by alkoxycarbonylation as disclosed herein.

The following examples will more clearly point out and demonstrate the improved process of this invention.

EXAMPLE 1

The following example is a repeat of Example 1 in U.S. Pat. No. 3,397,225 issued to Fenton. The results are representative of the results obtained in several unsuccessful attempts to duplicate the results of that example in the Fenton patent.

Into a 750 ml. Teflon-lined pressure vessel were placed 2gm (11.27mMoles)$PdCl_2$, 80gm (595mMoles)$CuCl_2$, and 600 ml methanol. The vessel was pressurized with ethylene to 600 p.s.i.g. and CO was added to increase the pressure to 1200 p.s.i.g. The bomb contents were stirred while heating to 120° C. and held at that temperature for four hours. At the end of the four hour period, the final pressure was 660 p.s.i.g., indicating absorption or reaction of the gaseous reactants. The bomb was cooled, depressurized and opened, and the liquid contents filtered to separate insoluble cuprous chloride. The filtrate consisted of 413 gm of solution. The vented gas contained 19mMoles $CO_2$.

The filtrate was distilled to obtain 373 gm of a product having a boiling point of 65° C. at 760mm Hg pressure. The pot residue consisted of 19 gm of material.

Gas-liquid chromotography separations were carried out on a 20 foot × ⅛ inch column of 20% UCON-50HB 2000X on a Firebrick R 40–60 mesh support. This type of column allows the methyl propionate to be separated from any methyl acrylate present in the distillate.

TABLE 1

GLC ANALYSIS OF REACTION PRODUCTS

| | Area, % Crude Product | Area, % Distillate | Area, % Pot Residue |
|---|---|---|---|
| $H_2O$ | 6.65 | 5.24 | 37.05 |
| Methanol | 90.48 | 93.51 | 15.16 |
| Unknown | — | — | .17 |
| Methyl Propionate | .62 | .57 | .02 |
| Methyl Acrylate | .04 | .03 | .03 |
| Methyl β-methoxy-propionate | 2.15 | .65 | 42.17 |
| β-Methoxypropionic acid | — | — | 1.45 |
| High Boilers | .06 | — | 3.94 |

The results show that while almost no methyl acrylate is produced by the reaction, methyl β-methoxypropionate is however produced, along with various undesirable by-products. Additionally, the above procedure does not allow catalyst to be recycled in a convenient manner.

The following examples demonstrate the improved process and detail some of the steps in that process. In all cases, the gas-liquid chromotography was carried out on the column described in Example 1, or on a 5 foot × ⅛ inch column of 5% FFAP coated onto a POROPACK Z 50–80 mesh support.

EXAMPLE 2

Into a 1000 ml pressure reactor are placed 0.5 gm (2.8mMole)$PdCl_2$, 3.1gm (11.4mMole) $HgCl_2$, and 27gm (200mMoles) $CuCl_2$. The catalyst is dissolved by adding 20gm anhydrous methanol and 150gm methyl β-methoxypropionate. The reactor is pressurized with 600 p.s.i.g. of a 50% ethylene/50% carbon monoxide gas mixture and the contents stirred while heating to 50° C. The temperature is maintained at 50° C. while the stirring is continued for an additional 2.5 hours. The final pressure in the reactor is 400 p.s.i.g., indicating completion of reaction. After venting unreacted ethylene/carbon monoxide, the reactor is pressurized with 300 p.s.i.g. of nitrogen and heated, while stirring, to 100° C. Oxygen is added in 50 p.s.i.g. increments to regenerate the catalyst. When no further drop in pressure is noted, regeneration is completed.

The bomb is cooled, depressurized and opened. Analysis of the solution before and after reaction indicates that methanol had reacted with ethylene and carbon monoxide to form methyl β-methoxypropionate. 50gm of $H_2O$/MeOH/product were removed by distillation under reduced pressure. To the remaining catalyst solution are added 20gm methanol and 30gm methyl β-methoxypropionate. This catalyst solution is recycled and reacted gain with ethylene and carbon monoxide by the above procedure. Analysis of the product again shows formation of the desired ester, and illustrates the feasibility of using β-alkoxy-substituted ester as a co-solvent for the catalyst system.

The above results are summarized in Table 2.

TABLE 2

GLC ANALYSIS (AREA, %)

| | | $H_2O$ | Methanol | Methyl β-Methoxypropionate |
|---|---|---|---|---|
| First Run | before reaction | 0.41 | 15.3 | 83.5 |
| | after reaction | 2.70 | 6.9 | 88.6 |
| Using recycled catalyst | before reaction | 1.40 | 19.0 | 79.2 |
| | after reaction | 3.72 | 12.0 | 82.9 |

EXAMPLE 3

A. REACTION

Into a 750 ml, Teflon-lined pressure vessel are placed 1.5gm (8.5mMoles) $PdCl_2$, 9.3gm (34.3mMoles) $HgCl_2$ and 162gm (1200mMoles) $CuCl_2$. The catalyst is dissolved in 225 ml methanol and 225 ml sulfolane (total weight = 623gm). The bomb contents are pressurized with 600 p.s.i.g. of a 75% ethylene/25% carbon monoxide gas mixture. The bomb contents are stirred while heating to 50° C. and are held at this temperature for the duration of the reaction. Ethylene and carbon monoxide are fed into the reactor to maintain the pressure at 600 p.s.i.g. After 130 minutes reaction time, the unreacted ethylene and carbon monoxide are vented, the bomb is pressurized with air to 800 p.s.i.g. and the contents are stirred at essentially ambient temperature. The pressure drops quickly to about 650 p.s.i.g. indicating catalyst regeneration. Oxygen is added to bring the pressure back up to 800 p.s.i.g. This procedure is repeated until no more pressure drop is noted. The bomb is then depressurized, opened and liquid contents analyzed by gas-liquid chromatography, which shows that 282mMoles of methyl β-methoxypropionate are formed with only trace levels of by-products.

B. SEPARATIONS

Crude product solution from the above reaction is combined with solutions from other similar reactions and is fed into a distillation flask heated to about 90° C. and evacuated to about 100 mm Hg. The overhead material consists of water, methanol and methyl β-methoxypropionate. The bottoms consist of a sulfolane slurry of catalyst. This slurry is admixed with the theoretical amount of methanol to afford a homogenous solution.

C. RECYCLE

600gms of the recycled catalyst solution are reacted with ethylene and carbon monoxide as described in Part A, above. Analysis of the crude product by gas-liquid chromotography indicates that 210mMoles of methyl β-methoxypropionate are formed. This solution may be treated as in Part B and recycled further. No β-methoxypropionic acid or other high boiling by-products are formed during the distillations. Gas-liquid chromotography analysis of the recycled catalyst solution indicates that some methyl β-methoxypropionate is present. This illustrates the feasibility of methyl β-methoxypropionate/sulfolane mixtures as media for the reaction, and also the advantage of such a system in that complete removal of the β-alkoxy substituted ester is not necessary prior to recycling.

Catalyst data is summarized in Table 3.

TABLE 3

| CATALYST SOLUTION SAMPLE | GLC ANALYSIS (AREA, %) | | | |
|---|---|---|---|---|
| | $H_2O$ | METH-ANOL | METHYL β-METHOXY-PROPIONATE | SULFOLANE |
| Fresh Catalyst Solution | <1% | 61.9 | — | 32.4 |
| Solution After First Cycle | 3.99 | 55.27 | 6.19 | 31.37 |
| Recycled Catalyst Solution | 1.52 | 60.6 | .63 | 34.11 |
| Solution After Second Cycle | 3.58 | 54.0 | 5.88 | 33.2 |

EXAMPLE 4 a. A 1000 ml glass-lined pressure reactor is charged with 0.5gm (2.8mMoles) $PdCl_2$, 27gm (200mMoles) $CuCl_2$, and 250 ml anhydrous methanol. Ethylene is added to 300 p.s.i.g., and carbon monoxide to bring the pressure up to 600 p.s.i.g. The reactor is heated to 120° C. and stirred at this temperature for 4 hours. A 5 ml aliquot of n-heptane is introduced as an internal reference for gas-liquid chromotography analysis.

b. Example similar to (a.) except that the reaction temperature is kept at 50° C. for 4 hours.

c. Example similar to (a.) except that 3.1gms (11.4mMoles) $HgCl_2$ are added as a co-catalyst for $PdCl_2$. Reaction temperature kept at 120° C. for 4 hours.

d. Example similar to (a.) except that 3.1 gms (11.4mMoles) $HgCl_2$ are added as a co-catalyst for $PdCl_2$. Reaction temperature kept at 50° C. for 4 hours.

e. Example similar to (a.) except that 2.2gms (11.4mMoles) $SnCl_2$ are added as a co-catalyst for $PdCl_2$. Reaction temperature kept at 120° C. for 4 hours.

f. Example similar to (a.) except that 2.2gms (11.4mMoles) $SnCl_2$ are added as a co-catalyst for $PdCl_2$. Reaction temperature kept at 50° C. for 4 hours.

Results for the above examples are given in Table 4.

TABLE 4

| | CATALYST (mMoles) | TEMP. °C. | $H_2O$ AREA, % | DIMETHYL ETHER/ METHYL CHLORIDE AREA, % | METHANOL AREA, % | METHYL PROPIONATE AREA, % | METHYL PROPIONATE mMoles | METHYL βMETHOXYPROPIONATE AREA, % | METHYL βMETHOXYPROPIONATE mMoles |
|---|---|---|---|---|---|---|---|---|---|
| a. | 2.8 $PdCl_2$ 200.0 $CuCl_2$ | 120 | 5.1 | 6.0 | 83.8 | 0.29 | 9.5 | 3.2 | 69.6 |
| b. | 2 $PdCl_2$ 200.0 $CuCl_2$ | 50 | 0.9 | 0.5 | 92.4 | 0.91 | 27.6 | 3.28 | 61.5 |
| c. | 2.8 $PdCl_2$ 11.4 $HgCl_2$ 200.0 $CuCl_2$ | 120 | 6.1 | 9.6 | 79.1 | 0.0 | 0.0 | 3.7 | 84.0 |
| d. | 2.8 $PdCl_2$ 11.4 $HgCl_2$ 200.0 $CuCl_2$ | 50 | 0.8 | 0.7 | 91.5 | 0.0 | 0.0 | 5.0 | 89.1 |
| e. | 2.8 $PdCl_2$ 11.4 $SnCl_2$ 200.0 $CuCl_2$ | 120 | 5.3 | 7.9 | 81.8 | 1.3 | 6.9 | 3.5 | 86.0 |
| f. | 2.8 $PdCl_2$ 11.4 $SnCl_2$ 200.0 $CuCl_2$ | 50 | 1.2 | 0.9 | 91.0 | 1.64 | 8.2 | 4.38 | 85.6 |

EXAMPLE 5 a. A 1000 ml glass-lined pressure reactor is charged with 0.5gm (2.8mMoles) $PdCl_2$, 27gm (200mMoles) $CuCl_2$ and 160gm anhydrous methanol. Propylene is charged to 100 p.s.i.g. and sufficient carbon monoxide added to raise the pressure to 600 p.s.i.g. The reactor is heated to 50° C. and the contents stirred for 3 hours at this temperature. Gas-liquid chromotography analysis of the reaction medium shows the presence of 2.9gm (22mMoles) methyl β-methoxy-n-butyrate.

b. Same as in (a.), except that 3.1gms (11.4mMoles) $HgCl_2$ are included in the catalyst charge. Gas-liquid chromotography analysis shows the formation of 9.1gm (69mMoles) of methyl β-methoxy-n-butyrate.

EXAMPLE 6 a. A 1000 ml Teflon-lined pressure reactor is charged with 1.2gm (6.7mMoles) $PdCl_2$, 7.4gm (27.3mMoles) $HgCl_2$, 131gm (970mMoles) $CuCl_2$, 313gm isopropanol and 120gm sulfolane. A gas mixture, consisting of 19.5% carbon monoxide and 80.5% ethylene is fed to the reactor at a rate of 880 ml/min. Excess unreacted carbon monoxide/ethylene is constantly bled from the vapor space above the liquid level at a rate so as to maintain the pressure in the reactor at 150 p.s.i.g. The contents are heated to 50° C. and stirred for 60 min. after which the gas feed is shut off and the contents removed from the reactor. Gas-liquid chromotography shows the presence of 3.4% product, identified by Mass Spectral analysis as isopropyl β-isopropoxypropionate.

EXAMPLE 7

A 1000 ml Teflon-lined pressure reactor is charged with 1.2gm (6.8mMoles) $PdCl_2$, 7.4gm (27.3mMoles) $HgCl_2$, 130gm (967mMoles) $CuCl_2$, 180gm sulfolane and 240 gm anhydrous ethanol. A gas mixture, consisting of 24.1% carbon monoxide and 75.9% ethylene, is fed to the reactor through a glass frit tube extending beneath the liquid level at a rate sufficient to maintain the pressure in the reactor at 150 p.s.i.g. Excess, unreacted carbon monoxide/ethylene is constantly bled from the vapor space above the liquid level at a rate of 238 ml/min. The contents of the reactor are heated to 50° C. and stirred for 60 minutes at this temperature, after which the gas feed is shut off and the contents removed from the reactor.

Analysis of both the gaseous vent and the liquid phase by gas-liquid chromotography indicates that ethyl β-ethoxypropionate is the primary reaction product (183mMoles) and carbon dioxide the only significant by-product (19mMoles). No ethyl propionate or other by-products are noticed in the product solutions. This demonstrates the feasibility of producing β-alkoxypropionates in high selectivites on ethylene (ca. 100%) and carbon monoxide (ca. 90%).

We claim:

1. A process for the synthesis of α,β-unsaturated carboxylic acid esters from a β-alkoxycarboxylic acid ester obtained by the alkoxycarbonylation of an olefin having from 2 to about 15 carbon atoms, said process comprising the steps of:
   a. contacting said olefin and carbon monoxide with an alcohol having 1 to about 10 carbon atoms in the presence of a catalytic amount of a salt of a platinum group metal in an elevated oxidation state and a salt of a multivalent metal having an oxidation potential more positive than said platinum group metal, essentially in the absence of oxygen at a temperature from about 0° to about 250° C. and a pressure from atmospheric to about 2500 p.s.i.g., to reduce said multivalent metal to a lower oxidation state and thereby form the ester, and
   b. regeneration of the catalyst by reoxidation at a temperature from 0° to about 250° C., the improvements wherein (1) the alkoxycarbonylation reaction is carried out in the presence of a catalyst comprising at least one salt of said platinum group metal, at least one salt of a metal selected from the group consisting of mercury (II) and tin (II), and additionally at least one salt of a multivalent metal having an oxidation potential more positive than said platinum group metal, (2) the β-alkoxycarboxylic acid ester formed is substantially isolated from the catalyst/reactants mixture and (3) said isolated β-alkoxycarboxylic acid ester is cracked to the corresponding α,β-unsaturated carboxylic acid ester.

2. A process for synthesis of α,β-unsaturated carboxylic acid esters from a β-alkoxycarboxylic acid ester obtained by the alkoxycarbonylation of an olefin having from 2 to about 15 carbon atoms, said process comprising the steps of:
   a. contacting said olefin and carbon monoxide with an alcohol having 1 to about 10 carbon atoms in the presence of a catalytic amount of a salt of a platinum group metal in an elevated oxidation state and a salt of a multivalent metal having an oxidation potential more positive than said platinum group metal, essentially in the absence of oxygen at a temperature from about 0° to about 250° C., and a pressure from atmospheric to about 2500 p.s.i.g., to reduce said multivalent metal to a lower oxidation state and thereby form the ester, and
   b. regeneration of the catalyst by reoxidation at a temperature from 0° to about 250° C., the improvements wherein (1) a reaction solvent system is employed, said solvent system having a solvent with a boiling point higher than that of the β-alkoxycarboxylic acid ester, (2) regeneration is performed prior to isolation of the β-alkoxycarboxylic acid ester from the catalyst/reactants mixture, (3) the β-alkoxycarboxylic acid ester formed by the alkoxycarbonylation reacton is substantially isolated from the catalyst/reactants mixture in a third step, and (4) said isolated β-alkoxycarboxylic acid ester is cracked to the corresponding α,β-unsaturated carboxylic acid ester.

3. A process for the synthesis of α,β-unsaturated carboxylic acid esters from a β-alkoxycarboxylic acid ester obtained by the alkoxycarbonylation of an olefin having from 2 to about 15 carbon atoms, said process comprising the steps of:
   a. contacting said olefin and carbon monoxide with an alcohol having 1 to about 10 carbon atoms in the presence of a catalytic amount of a salt of a platinum group metal in an elevated oxidation state and a salt of a multivalent metal having an oxidation potential more positive than said platinum group metal, essentially in the absence of oxygen at a temperature from about 0° to about 250° C., and a pressure from atmospheric to about 2500 p.s.i.g., to reduce said multivalent metal to a lower oxidation state and thereby form the ester, and
   b. regeneration of the catalyst by reoxidation at a temperature from 0° to about 250° C., the improvements wherein (1) the regeneration is performed prior to isolation of the β-alkoxycarboxylic acid ester from the catalyst/reactants mixture, (2) the β-alkoxycarboxylic acid ester is substantially isolated from the catalyst/reactants mixture following the regeneration step, and (3) said isolated β-alkoxycarboxylic acid ester is cracked to the corresponding α,β-unsaturated carboxylic acid ester.

4. In a process for the synthesis of α,β-unsaturated carboxylic acid esters from a β-alkoxycarboxylic acid ester obtained by the alkoxycarbonylation of an olefin having from 2 to about 15 carbon atoms, said process comprising the steps of:
   a. contacting said olefin and carbon monoxide with an alcohol having 1 to about 10 carbon atoms in the presence of a catalytic amount of a salt of a platinum group metal in an elevated oxidation state and a salt of a multivalent metal having an oxidation potential more positive than said platinum group metal, essentially in the absence of oxygen at a temperature from about 0° to about 250° C., and a pressure from atmospheric to about 2500 p.s.i.g., to reduce said multivalent metal to a lower oxidation state and thereby form the ester, and
   b. regeneration of the catalyst by reoxidation at a temperature from 0° to about 250° C., the improvements wherein (1) the alkoxycarbonylation reaction is carried out in the presence of a catalyst comprising at least one salt of said platinum group metal, at least one salt of a metal selected from the group consisting of mercury (II) and tin (II), and additionally at least one salt of a multivalent metal having an oxidation potential more positive than said platinum group metal, (2) in a solvent system comprising said alcohol, said β-alkoxycarboxylic acid ester and a solvent having a boiling point higher than that of the β-alkoxycarboxylic acid ester, (3) regeneration is performed prior to isolation of the β-alkoxycarboxylic acid ester from the catalyst/reactants mixture, (4) the β-alkoxycarboxylic acid ester is substantially isolated from the catalyst/reactants mixture in a third step and (5) said isolated β-alkoxycarboxylic acid ester is cracked to the corresponding α,β-unsaturated carboxylic acid ester.

5. The process of claim 1 wherein the catalyst regeneration step is carried out by reoxidation with air, oxygen, or air and oxygen at a pressure from atmospheric to about 1500 p.s.i.g.

6. The improved process of claim 1 wherein the mercury (II) salt is selected from the group consisting of halide, sulfates, nitrates, ($C_1$-$C_5$) carboxylates and chelates selected from the class consisting of acetyl acetonate, citric acid and ethylene diamine tetraacetic acid.

7. The improved process of claim 1 wherein the tin (II) salt is selected from the group consisting of halides, sulfates, nitrates ($C_1$-$C_5$) carboxylates and chelates selected from the class consisting of acetyl acetonates, citric acid and ethylene diamine tetraacetic acid.

8. The improved process of claim 1 wherein the ratio of olefin to carbon monoxide is about 3:1.

9. The improved process of claim 4 wherein the alkoxycarbonylation process is carried out at a temperature in the range of 10° to about 85° C. and a pressure range of 75 to about 800 p.s.i.g.

10. The improved process of claim 1 wherein the alkoxycarbonylation process is carried out at a temperature in the range of 25° to about 75° C., and a pressure range of 150 to about 600 p.s.i.g.

11. The improved process of claim 1 wherein the platinum group metal is palladium and the multivalent metal is copper.

12. The improved process of claim 2 wherein the solvent having a boiling point higher than that of the β-alkoxycarboxylic acid ester is a sulfone present in 30 to 200 parts per 100 parts of the alcohol.

13. The improved process of claim 12 wherein the sulfone is sulfolane.

* * * * *